United States Patent
Schermeier et al.

(10) Patent No.: US 8,012,099 B2
(45) Date of Patent: Sep. 6, 2011

(54) PROCESS AND DEVICE FOR OPERATING A RESPIRATION SYSTEM

(75) Inventors: Olaf Schermeier, Lübeck (DE); Thomas Klessaschek, Lübeck (DE); Marco Zelk, Hamberge (DE); Bernd Kellner, Lübeck (DE)

(73) Assignee: Dräger Medical GmbH, Lübeck (DE)

(*) Notice: Subject to any disclaimer, the term of this patent is extended or adjusted under 35 U.S.C. 154(b) by 1384 days.

(21) Appl. No.: 11/534,572

(22) Filed: Sep. 22, 2006

(65) Prior Publication Data
US 2007/0175471 A1    Aug. 2, 2007

(30) Foreign Application Priority Data
Sep. 24, 2005  (DE) .......... 10 2005 045 720

(51) Int. Cl.
A61B 5/08    (2006.01)
(52) U.S. Cl. .......... 600/538; 600/529; 128/204.18; 128/204.24
(58) Field of Classification Search .......... 600/529, 600/531, 532, 538–543; 128/204.18–204.26
See application file for complete search history.

(56) References Cited

U.S. PATENT DOCUMENTS

| | | | |
|---|---|---|---|
| 5,701,894 A * | 12/1997 | Cherry et al. | 600/300 |
| 6,190,326 B1 * | 2/2001 | McKinnon et al. | 600/529 |
| 2002/0100474 A1 * | 8/2002 | Kellner et al. | 128/200.24 |
| 2002/0144682 A1 * | 10/2002 | Kruger et al. | 128/204.18 |
| 2004/0187871 A1 | 9/2004 | Kimmel et al. | |

FOREIGN PATENT DOCUMENTS

| | | |
|---|---|---|
| DE | 199 51 579 C1 | 4/2001 |
| DE | 20113789 U1 | 6/2002 |
| DE | 201 21 627 U1 | 2/2003 |
| EP | 1731089 A | 12/2006 |
| WO | WO 02/078775 A | 10/2002 |
| WO | WO 2002/078775 * | 10/2002 |
| WO | WO 2005/002655 * | 1/2005 |
| WO | WO 2005/002655 A | 1/2005 |

* cited by examiner

Primary Examiner — Charles A Marmor, II
Assistant Examiner — Michael D'Angelo
(74) Attorney, Agent, or Firm — McGlew and Tuttle, P.C.

(57) ABSTRACT

A process for operating a respiration system (3) makes it possible, rapidly and with simple means, to operate the respiration system (3). The system and method use respiratory flow sensor-specific, patient- and/or treatment-related operating data and a respiratory flow sensor (1). A reading unit present in the respiration system (3) reads the contents of a transponder (2) connected to the respiratory flow sensor (1), so that the respiration system (3) is ready to operate only after the operating data have been read.

17 Claims, 1 Drawing Sheet

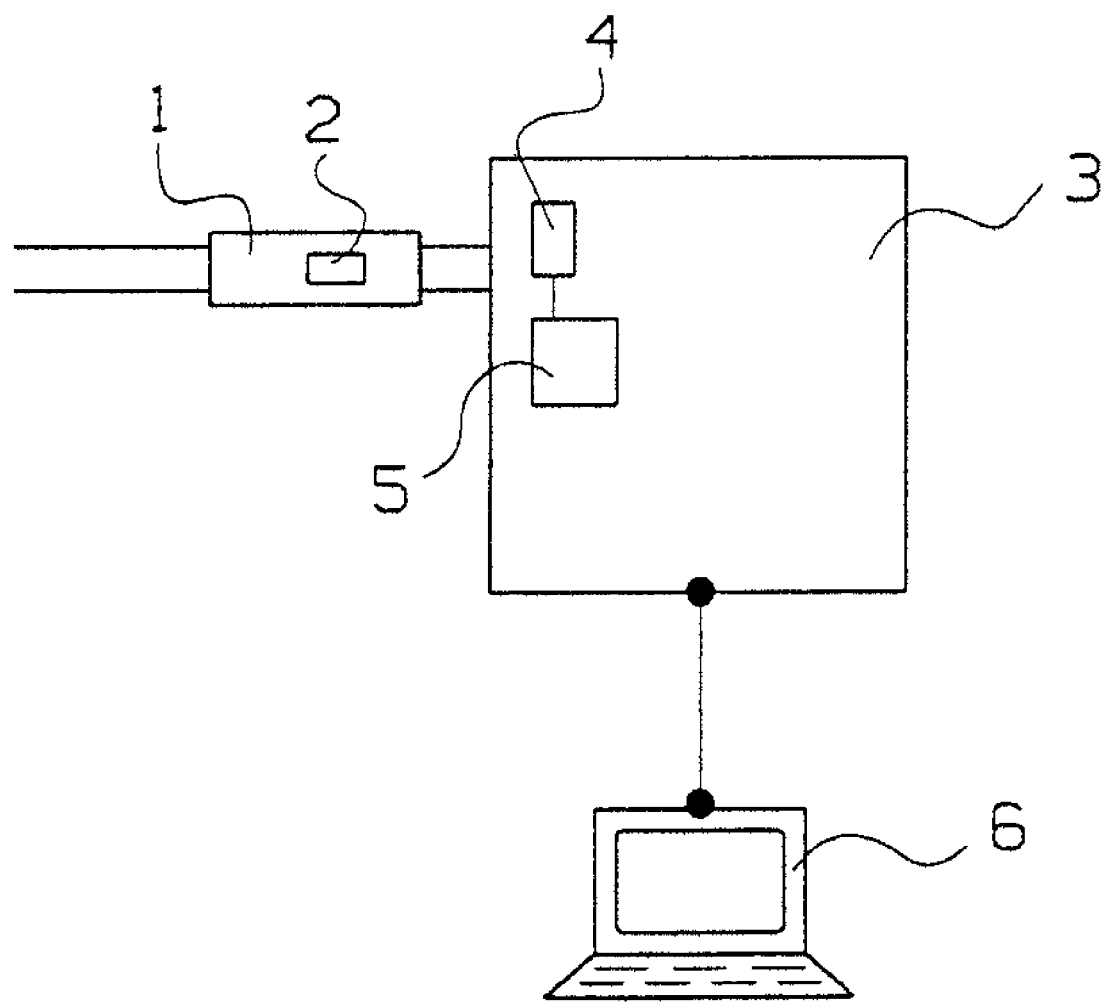

PROCESS AND DEVICE FOR OPERATING A RESPIRATION SYSTEM

CROSS REFERENCE TO RELATED APPLICATIONS

This application claims the benefit of priority under 35 U.S.C. §119 of German Patent Application DE 10 2005 045 720.7 filed Sep. 24, 2005, the entire contents of which are incorporated herein by reference.

FIELD OF THE INVENTION

The present invention pertains to a process for operating a respiration system (also known as ventilator system) by means of a respiratory flow sensor and to a device for operating a respiration system.

BACKGROUND OF THE INVENTION

DE 201 13 789 U1 discloses a medical device with a base unit, with a control unit and at least with a replaceable auxiliary device, which can be connected to the base unit, wherein the base unit contains at least one transponder polling device for wireless communication with a transponder in the auxiliary device, which transponder transmits information on the auxiliary device to the polling device upon request by the latter. The information is used by the base unit to determine operating parameters for the base unit.

During the operation of respiration systems, it is necessary to take over respiratory flow sensor-specific as well as optionally patient- and treatment-specific data into the respiration system rapidly and possibly not manually, so that the respiration can be adapted to the particular concrete conditions.

SUMMARY OF THE INVENTION

Thus, the object of the present invention is to provide a process and a corresponding device that make it possible, rapidly and with simple means, to operate a respiration system with current operating data that are relevant for the operation.

According to the invention a process is provided for operating a respiration system by means of a respiratory flow sensor. A reading unit present in the respiration system reads the contents of a means for storing operating data for the respiration system. This means is connected to the respiratory flow sensor, in a wireless manner, so that the respiration system is only ready to operate after the operating data have been read.

The operating data may comprise identification data and/or quality data of the respiratory flow sensor for the respiration system. Such data are compared by the respiration system with identification data and/or quality data stored there, so that the respiration system is ready to operate only when the identification data compared agree.

After the operation of the respiration system, current operating data of the respiration system may be transferred into the means for storing operating data and are stored there. Such means is advantageously connected to the respiratory flow sensor, in a wireless manner.

The operating data may comprise patient-related and/or treatment-related data.

The operating data may comprise respiratory flow sensor-specific data, especially actual release data, so that the measured values of the respiratory flow sensor are used in the respiration system for the operation of the respiration system in a correspondingly corrected form.

The means for storing operating data, which means is connected to the respiratory flow sensor, may be a writable and/or readable transponder. The reading unit present in the respiration system may be combined with a writing unit for the transponder.

The respiratory flow sensor may be a hot-wire anemometer with a sensor housing made of a plastic and the means for storing operating data is connected to the sensor housing by means of a bonding agent.

The respiration system is advantageously an anesthesia apparatus or respirator.

According to another aspect of the invention, a device for a respiration system and a respiration system are provided in which the system is equipped with a reading unit and preferably with a wiring unit. The device has a respiratory flow sensor that is equipped with an associated means, which can be read in a wireless manner, for storing operating data for the respiration system, especially with a transponder.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

BRIEF DESCRIPTION OF THE DRAWINGS

In the drawings:

The only FIGURE is a schematic view show of an arrangement for carrying out the process in accordance with the invention.

DESCRIPTION OF THE PREFERRED EMBODIMENTS

Referring to the drawings in particular, an exemplary embodiment will be explained below by means of the only FIGURE, which schematically shows an arrangement for carrying out the process with a respiratory flow sensor 1 in a breathing gas line for respirating (also known as ventilating) a patient, wherein the respiratory flow sensor 1 is designed especially as a hot-wire anemometer, which is known per se, and is equipped at the sensor housing with a transponder (operating data storage device) 2, which is attached by bonding, for example, on the outside.

The respiration system 3, for example, an anesthesia apparatus, is equipped with a transponder communication unit 4 with an antenna and with a reading and writing unit 5, which is connected to the operating electronic unit of the respiration system 3, so that especially respiratory flow sensor-specific operating data of the transponder 2 can be read and taken over from the respiration system 3 in a wireless manner via the transponder communication unit 4 and current operating data of the respiration system 3 can be stored in the respiratory flow sensor 1. The respiration system 3 is controlled via the operating or processor unit 6, for example, from a central workplace. If the operating or processor unit 6 communicates with a higher-level data and information system, the detected and transmitted operating data can be integrated in a global hospital documentation system or in ordering procedures after corresponding use times of the respiratory flow sensor 1 or according to operating states.

After the start of the respiration system 3 via the operating or processor unit 6, the human operator selects a certain respiration mode for the patient being respirated by means of the respiration system 3. The reading and writing unit 5 then uses the patient- and/or treatment-related data and identification data, including data relevant for the current quality, of the respiratory flow sensor 1 for the respiration system 3, which data are stored in the transponder 2 in the respiratory flow sensor 1, so that all the necessary information will then be available in the respiration system 3 to begin or optimize the respiration. No respiration begins in case of unallowed or unaccepted respiratory flow sensors 1, and a corresponding alarm or display is generated on the respiration system 3.

After the end of respiration, after preset time intervals or upon a corresponding command of the human operator of the respiration system 3, current operating data of the respiration system 3 are transferred into the memory of the transponder 2 via the reading and writing unit 5 and via the transponder communication unit 4.

Alternatives to the RFID (Radio Frequency Identification) system with an RFID transponder/tag and with an RFID reader, which is used in the example, are systems with bar codes and optical scanners for reading corresponding magnetic systems as well as other wireless inductive and capacitive systems, which are known per se.

The respiratory flow sensor-specific operating data also comprise actual release (unblocking) data, which are stored in the memory of the transponder 2 and are made available to the respiration system 3 upon a corresponding request (after polling) by the respiration system 3. The quality of the actually measured data of the sensors may be improved by an actual release, such that a correction of the measured data is performed via an update of the operating data of the respiratory flow sensor: An example for this would be measured data normally located outside of a defined tolerance range and not used, but which could be used for measurement evaluation, if actually redefined as usable by the actual release of operating data of the respiratory flow sensor. The updated selection and determination of allowed and accepted measured data is especially important, because they interfere with internal control loops and control circuits of the respiration system 3.

While specific embodiments of the invention have been shown and described in detail to illustrate the application of the principles of the invention, it will be understood that the invention may be embodied otherwise without departing from such principles.

What is claimed is:

1. A process for operating a respiration system, the process comprising:
   providing respiration system with a respiratory flow sensor;
   providing an operating data storage device connected to said respiratory flow sensor, said operating data storage device being readable in a wireless manner;
   providing a reading unit in the respiration system;
   reading the contents of said operating data storage device for the respiration system, so that said respiration system is ready to operate only after the operating data have been read, wherein the operating data comprise identification data and/or quality data of said respiratory flow sensor for said respiration system, which data are compared by said respiration system with stored identification data and/or quality data, so that said respiration system is ready to operate only when the compared identification data agree;
   selecting said at least one patient respiration mode; and
   operating said respiration system such that said at least one patient respiration mode is executed after reading said contents of said operating data storage device, wherein a patient is respirated with said respiration system based on said contents of said operating data storage device, wherein said respiration system comprises at least one patient respiration mode, wherein an alarm or display is generated on said respiration system when said identification data and/or quality data of said respiratory flow sensor does not agree with said stored identification data and/or quality data, said respiration system not operating when said identification data and/or quality data of said respiratory flow sensor does not agree with said stored identification data and/or quality data.

2. A process in accordance with claim 1, wherein after the operation of said respiration system, current operating data of said respiration system are transferred into the means for storing operating data, which said means is connected to said respiratory flow sensor, in a wireless manner, and are stored.

3. A process in accordance with claim 1, wherein the operating data comprise patient-related and/or treatment-related data.

4. A process in accordance with claim 1, wherein the operating data comprise respiratory flow sensor-specific data or actual release data, so that the measured values of said respiratory flow sensor are used in said respiration system for the operation of said respiration system in a correspondingly corrected form.

5. A process in accordance with claim 1, wherein said operating data storage device, which is connected to said respiratory flow sensor, is a writable and/or readable transponder, and said reading unit present in said respiration system is combined with a writing unit for said transponder.

6. A process in accordance with claim 5, wherein said respiratory flow sensor is a hot-wire anemometer with a sensor housing made of a plastic and said transponder is connected to said sensor housing by means of a bonding agent.

7. A process in accordance with claim 1, wherein said respiratory flow sensor is a hot-wire anemometer with a sensor housing made of a plastic and said means for storing operating data is connected to said sensor housing by means of a bonding agent.

8. A process in accordance with claim 1, wherein said respiration system is an anesthesia apparatus or respirator, said respiration system comprising a tube element, said anesthesia apparatus or respirator comprising said reading unit, said tube element being connected to said anesthesia apparatus or respirator, said operating data storage device being arranged on said tube element.

9. A device for operating a respiration system, the device comprising:
   a respiration system reading unit;
   a respiratory flow sensor;
   an operating data storage device that can be read in a wireless manner by said respiration system reading unit, said operating data storage device for storing operating data for said respiration system; and
   a control means for controlling the respiration system such the respiration system is activated to respirate a patient after said respiration system reading unit processes said operating data, wherein the operating data comprise identification data and/or quality data of said respiratory flow sensor for said respiration system, and said data are compared by said respiration system with stored identification data and/or quality data, so that said respiration system is ready to operate only when the compared identification data and/or quality data agree.

10. A device according to claim 9, wherein said respiration system reading unit includes a wiring unit for writing data to said operating data storage device, said operating data storage device being a transponder.

11. A respiration system comprising:
a respiration system respiratory flow sensor;
an operating data storage device connected to said respiratory flow sensor, said operating data storage device being readable in a wireless manner;
a reading unit in the respiration system for reading data from said operating data storage device in a wireless manner;
a system control for releasing at least one mode of respiration of said respiration system for operation only after the operating data have been read via said reading unit, wherein said patient is respirated with said at least one mode of respiration based on said operating data, wherein the operating data comprise identification data and/or quality data of said respiratory flow sensor, and said data are compared by said system control with identification data and/or quality data, so that the respiration system is ready to operate only when the compared identification data and/or quality data agree.

12. A respiration system in accordance with claim 11, wherein after the operation of said respiration system, current operating data of said respiration system are transferred into the means for storing operating data, which said means is connected to said respiratory flow sensor, in a wireless manner, and are stored there.

13. A respiration system in accordance with claim 11, wherein the operating data comprise patient-related and/or treatment-related data.

14. A respiration system in accordance with claim 11, wherein the operating data comprise respiratory flow sensor-specific data or actual release data, so that the measured values of said respiratory flow sensor are used in said respiration system for the operation of said respiration system in a correspondingly corrected form.

15. A respiration system in accordance with claim 11, wherein
said operating data storage device is a transponder, which is connected to said respiratory flow sensor,
said transponder is a writable and/or readable transponder, and said reading unit is combined with a writing unit for writing to said transponder, wherein an alarm or display is generated on said respiration system when said identification data and/or quality data of said respiratory flow sensor does not agree with said stored identification data and/or quality data, said respiration system not operating when said identification data and/or quality data of said respiratory flow sensor does not agree with said stored identification data and/or quality data.

16. A respiration system in accordance with claim 15, wherein said respiratory flow sensor is a hot-wire anemometer with a sensor housing made of a plastic and said transponder is connected to said sensor housing by means of a bonding agent.

17. A respiration system in accordance with claim 11, wherein said respiration system further comprises an anesthesia apparatus or respirator and a tube element, said anesthesia apparatus or respirator comprising said reading unit, said tube element being connected to said anesthesia apparatus or respirator, said operating data storage device being arranged on said tube element.

* * * * *